(12) United States Patent
Yoon et al.

(10) Patent No.: US 7,205,283 B2
(45) Date of Patent: Apr. 17, 2007

(54) ANTISENSE OLIGONUCLEOTIDES THAT INHIBIT EXPRESSION OF HIF-1

(75) Inventors: Heejeong Yoon, Germantown, MD (US); Lingjun Mao, Hope, RI (US); Young Bok Lee, Rockville, MD (US); Chang-Ho Ahn, Potomac, MD (US); Xiaoming Jiang, Gaithersburg, MD (US)

(73) Assignee: Rexahn Corporation, Potomac, MD (US)

(*) Notice: Subject to any disclaimer, the term of this patent is extended or adjusted under 35 U.S.C. 154(b) by 505 days.

(21) Appl. No.: 10/766,185

(22) Filed: Jan. 28, 2004

(65) Prior Publication Data

US 2004/0152655 A1 Aug. 5, 2004

Related U.S. Application Data

(60) Provisional application No. 60/444,367, filed on Jan. 31, 2003.

(51) Int. Cl.
*A61K 31/70* (2006.01)
*C07H 21/04* (2006.01)
*C07H 21/02* (2006.01)
*C12N 5/00* (2006.01)
*C12Q 1/68* (2006.01)

(52) U.S. Cl. ............................ 514/44; 435/6; 435/375; 435/377; 536/24.1; 536/24.5

(58) Field of Classification Search .................. None
See application file for complete search history.

(56) References Cited

U.S. PATENT DOCUMENTS 6,222,018 B1   4/2001  Semenza
2004/0096848 A1*  5/2004  Thrue et al. .................. 435/6
2004/0220393 A1*  11/2004  Ward et al. .................. 536/23.1

OTHER PUBLICATIONS

Hypoxia-inducible factor: Achilles' heel of antiangiogenic cancer therapy (Review), Blagosklonny, M.V., International Journal of Oncology 19: 257-262 (2001).
Single-Step Method of RNA Isolation by Acid Guanidinium Thiocyanate-Phenol-Chloroform Extraction, Chomczynski, P. and Sacchi, N., Analytical Biochemistry 162: 156-159 (1987).
Activation of Vascular Endothelial Growth Factor Gene Transcription by Hypoxia-Inducible Factor 1, Forsythe, J.A., et al., Molecular and Cellular Biology, vol. 16, No. 9: 4604-4613 (1996).
The von Hippel-Lindau tumor suppressor protein, Ivan, M. and Kaelin, W.G., Jr., Current Opinion in Genetics & Development, 11: 27-34 (2001).
Targeting of HIF-a to the von Hippel-Lindau Ubiquitylation Complex by O2-regulated prolyl Hydorxylation, Jaakola, P., et al., Science 292: 468-472 (2001).
Regulation and Destabilization of HIF-1-a by ARD1-Mediated Acetylation, Jeong, J.W., et al., Cell, 111: 709-720 (2002).
Asparagine Hydroxylation of the HIF Transactivation Domain: A Hypoxic Switch, Lando, D., et al., Science 295: 858-861 (2002).
38. Ein neuer Zugang zu 2'-O-alkylribonucleosiden und Eigenschaften deren Oligonucleotide, Martin, v. P. Helvetica Chimica Acta 78: 486-504 (1995).
aHIF: the Missing Link between HIF-1 and VHL? Neckers, M. N., J. Nat'l. Cancer Inst., vol. 91, No. 2: 106-7 (1999).
HIF-1 and human disease: one highly involved factor, Semenza, G. L., Genes & Development 14: 1983-1991 (2000).
Regulation of Hypoxia-induced angiogenesis: a chaperone excorts VEGF to the dance, Semenza.G. I.., J. Clin. Investigation vol. 108, No. 1: 39-40 (2001).
Overexpression of Hypoxia-Inducible Factor 1a in Common Human Cancers and Their Metastases, Zhong, H. et al., Cancer Research 59: 5830-5835 (1999).

* cited by examiner

*Primary Examiner*—Sean McGarry
(74) *Attorney, Agent, or Firm*—Valerie E. Looper

(57) ABSTRACT

New antisense oligonucleotide compounds, RX-0047 and RX-0149, inhibit expression of HIF-1 and also induce cytotoxicity in several cancer cell lines.

5 Claims, 2 Drawing Sheets

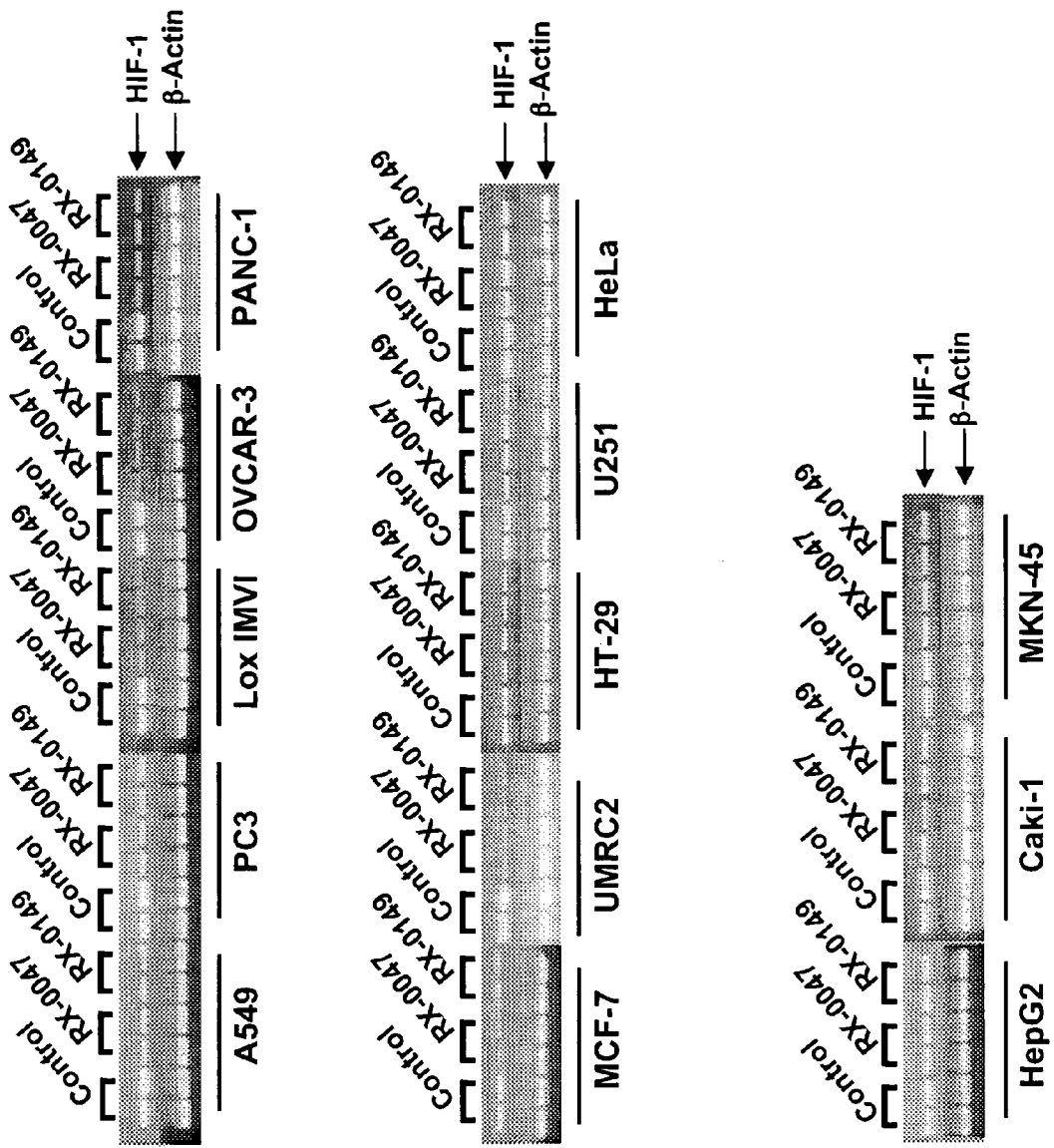
Fig. 1. RX-0047 and RX-0149 inhibit HIF-1 mRNA expression in various cancer cell lines

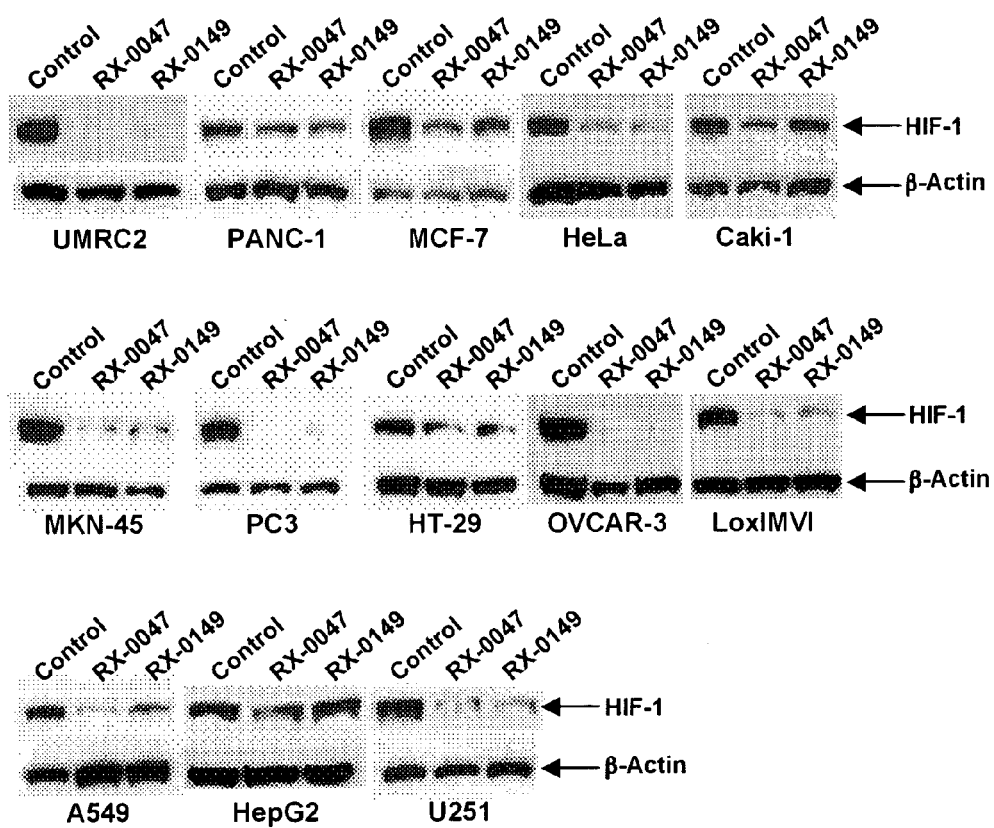
Fig. 2. Western blot analysis of inhibition of HIF-1 protein expression by RX-0047 and RX-0149

ANTISENSE OLIGONUCLEOTIDES THAT INHIBIT EXPRESSION OF HIF-1

RELATED APPLICATION

This application is a continuation-in-part of U.S. Ser. No. 60/444,367 filed Jan. 31, 2003. A corresponding PCT Application, Atty. Docket No. REX 7034, is filed concurrently herewith. Both applications are incorporated herein by reference as if set forth in full.

FIELD OF THE INVENTION

This invention relates to new antisense oligonucleotide compounds, RX-0047 and RX-0149, that inhibit expression of a human protein, HIF-1, and also induce cytotoxicity in several cancer cell lines.

BACKGROUND OF THE INVENTION

Tumors cannot grow without blood vessels that supply cancer cells with oxygen and nutrients (Blagosklonny, International J. Oncol., 2001 19: 257–262). Control of the hypoxic response in mammalian cells by the transcription factor, HIF-1 is one of the major regulators of cancer cell growth. HIF renders cells capable of surviving hypoxia and stimulating endothelial growth and it is upregulated in a broad range of cancers (Zhong et al., Cancer Res. 1999 59: 5830–5835). One of the most striking examples of the role of HIF in angiogenesis and tumor progression is the loss of function of the protein, VHL, which is a tumor suppressor gene that is mutated in most sporadic clear-cell renal carcinoma and in VHL disease. Therefore disruption of the HIF-1 pathway inhibits tumor growth, indicating HIF-1 as a potential anticancer target. Inhibition of HIF-1 is a mechanism-based anti-angiogenic strategy because it is the HIF-mediated response that drives tumor angiogenesis. U.S. Pat. No. 6,222,018 issued to Semenza, Apr. 24, 2001, relates to the nucleotide sequences encoding HIF-1. The specific oligonucleotides disclosed and claimed in the present invention were not disclosed in that patent.

BRIEF DESCRIPTION OF THE DRAWINGS

FIG. 1. RX-0047 and RX-0149 inhibit HIF-1 mRNA expression in various cancer cells FIG. 2. Western blot analysis of inhibition of HIF-1 protein expression by RX-0047 and RX-0149.

SUMMARY OF THE INVENTION

The present invention is directed to antisense oligonucleotides, which are targeted to a nucleic acid encoding HIF-1 (hypoxia-inducible factor 1), and which modulate the expression of HIF-1. Also provided is a method of inhibiting expression of HIF-1 in cells comprising contacting the cells with the oligonucleotide compounds and compositions of the invention. An advantage of the presently described oligonucleotides is that, in addition to inhibiting expression of HIF-1, they have a cytotoxic effect on several different cancer cell lines. The advantages of the present invention can be obtained by contacting cells of various cancer cell lines with an antisense compound that is specifically hybridizable to a site on the HIF-1 gene having the following sequence: 5' ttggacactggtggctcatt 3' at site 2,772 of HIF-1 gene (Genebank # NM001530) (Seq. Id. No. 1). Particularly preferred is RX-0047, comprising 5' aatgagccaccagtgtccaa 3' (Seq. Id. No. 2). Similar advantages can be obtained with a compound that is antisense to the sequence 5' gacttggagatgttagctcc 3' at site 1,936 of HIF-1 gene (Genebank # NM001530) (Seq. Id. No. 3). Particularly preferred is RX-0149, comprising, 5' ggagctaacatctccaagtc 3' (Seq. Id. No. 4). The contact occurs under conditions that allow the oligonucleotide to hybridize with the gene encoding HIF-1. After hybridization, the ability of the cells to produce HIF-1 is inhibited, and cancer cell viability is reduced.

DETAILED DESCRIPTION OF THE INVENTION

HIF (hypoxia-inducible factor) is a heterodimeric key transcription factor and activated by hypoxia. It not only mediates homeostatic responses including erythropoiesis, angiogenesis and glycolysis to hypoxia in mammals, but also facilitates tumor neovascularization and growth. It is composed of 2 different subunits, HIF-1α and HIF-1β which is also known as ARNT (Aryl Receptor Nuclear Translocator). These 2 subunits belong to the bHLH (basic helix-loop-helix) and PAS (Per, ARNT, Sim) family. The bHLH domain of these factors is responsible for dimerization through the two helices and for DNA binding through their basic domain. Two separate domains within HIF-1α and HIF-2α respond to hypoxia signaling pathways. The first is the oxygen-dependent degradation (ODD), which, at normoxia, is subject to post-translational modification by an oxygen-dependent prolyl hydroxylase (Jaakkola et al., Science, 2001, 292: 468–472). The hydroxylated proline promotes interaction of HIF with the VHL (von Hippel-Lindau) ubiquitin ligase complex, initiating rapid ubiquitination and subsequent HIF protein destruction via proteasome. Recent report indicated that asparagine hydroxylation of the HIF COOH-terminal transactivation domain (CAD) also plays an important role in proteasome-mediated HIF degradation by inhibiting interaction with the p300/CBP coactivator and reduces the transcriptional activity of HIF-1 during normoxia (Lando et al., Science, 2002, 295: 858–861). Therefore in conjunction with prolyl hydroxylase, asparagine hydroxylase works as a hypoxic switch regulated by $O_2$ level in the cell. During hypoxia, p42/p44 MAPK activity induces post-translational phosphorylation of HIF-1 and promotes the transcriptional activity of HIF-1. Recent reports show that along with the hydroxylation, ubiquitination and phosphorylation, acetylation plays an important role in regulation of HIF-1 stability (Jeong et al., Cell, 2002, 111: 709–720).

Under hypoxia, HIF-1α is not hydroxylated because the hydroxylase, which requires dioxygen for activity, is inactive and thus HIF-1α is not recognized by pVHL and accumulates in the cell. HIF-1α then translocates to the nucleus and dimerizes with the constitutively present HIF-1β subunit (Semenza, Genes & Development, 1985, 14: 1983–1991). The dimer then binds to the hypoxia responsive element (HRE) in target genes, resulting in their transactivation of genes such as erythropoitin, VEGF (Forsythe et al., Mol. Cell. Biol., 1996, 16: 4604–4613), platelet-derived growth factor-β (PDGF-β), glucose transporter (GLUT1) and nitrous oxide synthetase (Neckers, J. Natl. Cancer Ins., 1999, 91: 106–107). Certain hormones and growth factors also lead to increased levels of HIF-1α as well as mutations in certain oncogenes and tumor-suppressor genes, VHL for example, result in an increase in HIF-1α level (Ivan and Kaelin, Current Opinion in Genetics & Development, 2001, 11: 27–34). It will be interesting to determine whether hydroxylation or alternative mechanisms are involved in this hypoxia-independent HIF activation.

Several current strategies for cancer therapies that exploit the hypoxic microenvironment and response are as follows; 1) hypoxia-dependent drugs or gene-therapy vectors, 2) inhibition of HIF stability, 3) inhibition of transactivation by HIF, and 4) VEGF inhibitors.

Given the pivotal role of the HIF transcription factor in the development of cancers, it would be desirable to inhibit its operation during oncogenesis. However, it would also be desirable, to the extent possible, to avoid interrupting the family's roles in other aspects of cellular metabolism. One approach might be to identify the gene that encodes a likely transcription factor that expressed highly during hypoxia, and devise an antisense oligonucleotide that can be used to inhibit that gene's activity in the right context. The inventors have found that two antisense oligonucleotides both exhibit an enhanced ability to inhibit the production of protein by the HIF-1 gene, and further, induce cytotoxicity in a variety of cancer cell lines.

An antisense compound is a tool that can be used to introduce modifications into the nucleic acids found in living cells. The term "antisense" refers to the notion that nucleic acids "encode" proteins. That is, the sequence of nucleotides found in a given nucleic acid determines, among other things, what protein will be produced. A "sense" sequence for a full gene will yield a normal protein in the usual amount, in response to a given stimulus. A "sense" oligonucleotide will hybridize with a normal gene sequence, and will not affect the amount of, or properties of, the protein. A "nonsense" sequence will not yield a product, or may yield a non-functional product. For example, if a "nonsense" codon or oligomer is inserted into a gene, a truncated, non-functional protein may result. An "antisense" oligonucleotide will hybridize with a normal gene, but will yield a protein altered with respect to its structure, or amount. It has been found that antisense oligomers, that is antisense compounds that are relatively short, can be easily inserted into cells, where they alter gene function.

Antisense compounds are commonly used as research reagents for the exploration of gene function because they are able to alter gene expression with exquisite specificity, and may be used to elucidate the function of particular genes. Antisense compounds can be used, for example, to distinguish between functions of various members of a biological pathway.

Antisense oligonucleotides can be used to selectively block disease-causing genes, thereby inhibiting production of disease-associated proteins. Some antisense oligonucleotides have been safely and effectively administered to humans, and numerous clinical trials are presently underway. It is thus possible that oligonucleotides can be used to treat cells, tissues, and animals, especially humans. In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for a nucleic acid target and increased stability in the presence of nucleobases. The present invention employs oligomeric nucleotide compounds, particularly antisense oligonucleotides, which are targeted to a portion of a nucleic acid encoding HIF-1, and which modulate the expression of HIF-1. The oligonucleotide compounds are designed to specifically hybridize with one or more nucleic acids encoding HIF-1. One oligonucleotide, RX-0047, is targeted to a site on the HIF-1 gene having the following sequence: 5' ttggacactggtggctcatt 3' at site 2,772 of HIF-1 gene (Genebank # NM001530) (Seq. Id. No. 1). The sequence for the backbone of RX-0047 is complementary to this site. The other oligonucleotide, RX-0149, is targeted to a site in the coding region of the HIF-1 gene having the following sequence: 5' gacttggagatgttagctcc 3' at site 1,936 of HIF-1 gene (Genebank # NM001530) (Seq. Id. No. 3). The sequence for the backbone of RX-0149 is complementary to this site. The inventors have found that oligomers comprising either 5 or 10 nucleotides upstream and downstream from the sequence where the 20-mer of RX-0047 and RX-0149 were derived showed a measurable inhibition of HIF-1 mRNA expression. However, the inventors have found that, this oligonucleotide is more sensitive to variability, and that while 18-mer of RX-0149 showed some inhibition of HIF-1 mRNA expression, further truncation from either end resulted in a substantial loss of inhibition of HIF-1 mRNA expression. The oligomers comprising either 5 or 10 nucleotides upstream and downstream from the sequence where the 20-mer of RX-0047 and RX-0149 were derived demonstrated an inhibition of proliferation of cancer cells. The truncated versions of RX-0047 and RX-0149 which showed some inhibition of HIF-1 mRNA expression also showed an inhibition of cancer cell proliferation.

To target an antisense compound to a particular gene means to identify the nucleic acid sequence of interest, and select one or more sites within the nucleic acid sequence to be modified. Once the target site has been identified, an oligonucleotide is chosen which is sufficiently complementary to the target site so that it will hybridize specifically to the site, i.e., hybridize sufficiently well and with sufficient specificity, to give the desired effect.

As used herein, the phrase "nucleic acid encoding HIF-1" encompasses DNA encoding HIF-1, RNA (including pre-mRNA) transcribed from such DNA, and also cDNA derived from such RNA. The specific hybridization of an antisense oligomeric compound with its target nucleic acid interferes with the normal function of the nucleic acid. The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression, or production of, a protein. In the context of the present invention, "modulation" means either an increase (stimulation) or a decrease (inhibition) in the expression of a gene. For the present purposes, the gene encoding HIF-1 is modulated so that expression of HIF-1 is inhibited.

In the context of this invention, "to hybridize" means to hydrogen bond, which may be via Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 10 to about 30 nucleobases. Particularly preferred are antisense oligonucleotides comprising about 20 nucleobases (i.e. about 20 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N ($CH_3$)—$CH_2$— and —O—N($CH_3$)—$CH_2$—$CH_2$— [wherein the native phosphodiester backbone is represented as —O—P—O—$CH_2$—]. Also preferred are oligonucleotides having morpholino backbone structures.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow. Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-Me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. and are presently preferred base substitutions, even more particularly when combined with 2'-O-methoxyethyl sugar modifications.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding HIF-1, enabling sandwich and other assays to easily be constructed to exploit this fact. Hybridization of the antisense oligonucleotides of the invention with a nucleic acid encoding HIF-1 can be detected by means known in the art. Such means may include conjugation of an enzyme to the oligonucleotide, radiolabelling of the oligonucleotide or any other suitable detection means. Kits using such detection means for detecting the level of HIF-1 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

EXAMPLES

The following examples illustrate the practice of various aspects of the present inventions. They do not limit the inventions, or the claims, which follow them.

Example 1

Growth of Cancer Cell Lines

Cancer cells used to determine the effect of oligonucleotide compounds were obtained from the following sources: Human OVCAR-3 (ovary), MCF-7 (breast, hormone-dependent), HeLa (cervix), PC3 (prostate), HepG2 (liver), and A549 (lung), HT-29 (colon), PANC-1 (pancreas), Caki-1 (kidney) from the American Type Culture Collection (ATCC) (Manassas, Va.); U251 (brain), from Riken Cell Bank (Japan); MKN-45 (stomach) from the German Collection of Microorganisms and Cell Cultures (DSMZ) (Germany); UMRC2 (kidney) and Lox IMVI (melanoma) from the United States National Cancer Institute (Bethesda, Md.). All cell lines except UMRC2, Caki-1 and PANC-1 were grown in RPMI1640 medium (Invitrogen, Carlsbad, Calif.) supplemented with 10% fetal bovine serum ("FBS"), 1 mM sodium pyruvate, 10 mM HEPES and 100 U/ml penicillin and 100 µg/ml streptomycin ("P/S"). UMRC2, Caki-1 and PANC-1 cells were maintained in Dulbecco's modified Eagle's medium ("DMEM", Invitrogen) supplemented with 10% FBS, P/S, 10 mM HEPES and 2 mM L-glutamine. All cells were incubated at 37° C. under humidified 5% $CO_2$.

Example 2

Synthesis of Oligonucleotides

Various nucleotide sequences found in the human HIF-1α gene coding region known as the open reading frame ("ORF") and 3' untranslated region ("3' UTR") were selected as targets, and the corresponding complementary oligonucleotides synthesized. The backbone of each oligonucleotide was modified during synthesis to introduce phosphorothioate linkages between nucleotides, except at the 3' and 5' ends, so that an antisense oligonucleotide resulted.

Oligonucleotides located in the coding region of HIF-1α were synthesized using 8909 Expedite DNA synthesizer from Applied Biosystems, Foster City, Calif. ("ABI"). The synthesis of phosphorothioates was conducted the same manner as for the corresponding phosphodiester oligonucleotides except the standard oxidation bottle was replaced by 0.2 M 3H-1,2-benzodithiole-3-one 1,1-dioxide in acetonitrile for the stepwise thiation of the phosphite linkages. After cleavage from the controlled pore glass column and deblocking in concentrated ammonium hydroxide, the oligonucleotide compound was heated in the presence of ammonium hydroxide at 55° C. overnight. The supernatant was transferred to a new tube and ammonium hydroxide was evaporated by Speedvac plus and UVS400 Universal Vacuum System (Thermo Savant, Holbrook, N.Y.). The oligonucleotide was precipitated with 75 mM NaOAc, pH 7.2 and 2.5 volumes of ethyl alcohol and washed once with ethyl alcohol. The oligonucleotide was dissolved in water and the oligonucleotide concentration was measured by UV spectrophotometer.

Example 3

Transfection

The day before transfection, cells were trypsinized, counted and plated. For 6 well-plate each well 2.5×10⁵ cells were plated so that they reach 50–90% confluency at the day of transfection. All the reagents and media used for transfection experiment were obtained from Invitrogen (Carlsbad, Calif.). The following solutions were prepared in sterile tubes: Solution A: for each transfection, a mixture of 2 μl (0.5 μg) DNA, 100 μl of serum free medium ("Opti-MEM") and 3 μl PLUS reagent was incubated at room temperature for 15 minutes. Solution B: for each transfection, a mixture of 2.5 μl of Lipofectamine Reagent and 100 μl of serum free medium (Opti-MEM). Solutions A and B were combined and incubated at room temperature for 15 minutes. For transfection, cells were washed once with 2 ml of serum free medium or PBS and 800 μl of serum free medium (Opti-MEM) were added to each well. The combined solution A and B was added to each well and mixed gently. Subsequently cells were incubated for 3 hours at 37° C., the medium was replaced with regular medium and incubated for the indicated time. For the standard LIPOFECTAMINE 2000 protocol, which was employed for RT-PCR and cytotoxicity experiments, cells were plated in 96-well plates the day before transfection in 100 μl of growth medium. For each well, an oligonucleotide sample was diluted in 25 μl OPTI-MEM reduced serum medium. Separately LIPOFECTAMINE 2000 reagent was diluted (1:50) in 25 μl OPTI-MEM for 5 minutes at room temperature. The oligonucleotide and reagent were mixed and incubated at room temperature for 20 minutes to allow complex formation, and then the complex was added directly to the cells in their growth medium and gently mixed. Subsequently cells were incubated for 4 hours at 37° C., and then the medium was replaced with regular medium and incubated for the indicated time.

Example 4

Inhibition of HIF-1α mRNA Expression by Antisense Oligonucleotides

The antisense oligonucleotides were then tested for their ability to down-regulate, or inhibit, the expression of mRNA encoding HIF-1α. The level of expression of HIF-1α mRNA in cells transfected with the antisense oligonucleotides was measured by RT-PCR analysis. Samples were taken at 2 hours after transfection (change of media), RNA was isolated and subjected to RT-PCR analysis.

UMRC2 cells (2.5×10⁵ cells per well) on a 6-well plate were transfected with the experimental oligonucleotides and the transfected cells were used to isolate total RNA. Total RNA was isolated by using RNA-STAT kit (TEL-TEST, Inc., Friendswood, Tex.), according to the supplier's manual [See also Chomczynski, P. and Sacchi, N in *Anal. Biochem.* 162: 156–159 (1987)]. Briefly, media were removed from the two 6-well plates and total 0.5 ml RNA-STAT solution was added and mixed by pipetting several times, and transferred to an eppendorf tube. 0.1 ml of chloroform was added to the tube, and the tube was shaken vigorously for 15 seconds, and then incubated for 3 minutes at room temperature before centrifugation at 14,000 rpm for 15 minutes at 4° C. The top layer was transferred to a new tube and 0.3 ml of isopropanol was added and incubated for 10 minutes at room temperature. Subsequently the RNA precipitate was centrifuged at 14,000 rpm for 10 minutes. The resulting pellet was washed with 70% ethanol, dried briefly and reconstituted with 20 μl water. RNA concentration was determined by spectrophotometer. RT reaction was carried out using M-MLV enzyme kit (Invitrogen). 5 μg of total RNA was used to synthesize cDNA in 20 μl RT reaction. First-strand cDNA was synthesized by incubating total RNA, oligo dT (0.5 mg) and dNTP (0.5 mM) mixture at 65° C. for 5 minutes and by quick-chilling on ice. First-strand buffer, 7.4 mM DTT and 1 μL M-MLV Reverse Transcriptase (200 units) was added to the above reaction mixture and incubated at 37° C. for 50 minutes and the enzyme inactivation was followed at 70° C. for 15 minutes. HIF-1 cDNA synthesized by RT reaction was measured by PCR using Sapphire RCR mix (SuperBio Inc., Seoul, Korea) with appropriate primers. For HIF-1α mRNA detection, primers, 5' GCACAGGCCACATTCACG 3' (Seq. Id No. 5) and 5' TGAAGATTCAACCGGTTTAAGGA 3' (Seq. Id No. 6). Beta-actin was used as an internal PCR control. Primers for beta-actin were 5' CCCATGCCATCCTGCGTCTG 3' (Seq. Id. No. 7) and 5' ACGGAGTACTTGCGCTCAG 3' (Seq. Id. No. 8). PCR products were analyzed on 1.5% agarose gel by electrophoresis.

A total of 124 oligonucleotides were initially screened, and the results from the preferred four are shown in Table 1 below. Each oligonucleotide was retested to confirm the down-regulation of mRNA expression level. Each reaction was performed in duplicate.

TABLE 1

| | | | | | |
|---|---|---|---|---|---|
| | | | Expression of HIF-1α mRNA Inhibited | | |
| Rexahn # | Region | Target site* | 5'-Sequence-3' | Seq. Id. No. | % Inhibition |
| RX-0047 | 3'UTR | 2772 | aatgagccaccagtgtccaa | 2 | 54 |
| RX-0073 | 3'UTR | 3195 | attgtgcaattgtggctacc | 9 | 28 |
| RX-0149 | Coding | 1936 | ggagctaacatctccaagtc | 4 | 57 |
| RX-0158 | Coding | 2217 | gtgatgatgtggcactagta | 10 | 40 |

*Genebank #NM001530

RX-0047, RX-0073, RX-0149 and RX-0158 are new sequences designed by the inventors. These were chosen as representatives from two regions found in the reference, the ORF and 3' UTR regions of the HIF-1α gene, both exhibiting the highest % inhibition for that region according to the test used in that reference. All of the new sequences exhibited enhanced % inhibition over the reference, using the test described herein. However, it was found that % inhibition did not correlate with cytotoxicity, as discussed in Example 6. Subsequently, two oligonucleotides that exhibited both high % inhibition of HIF-1 mRNA expression in UMRC2 cells and cytotoxicity were selected for testing in 12 other cancer cell lines. A list of the nucleotides tested is shown in Table 2, below.

TABLE 2

List of HIF-1 S-Oligonucleotides

| ID | 5'-Sequence-3' | start | length | Sequence Id. # |
|---|---|---|---|---|
| RX-0001 | ctccatggtgaatcggtccc | 251 | 20 | 11 |
| RX-0002 | gccggcgccctccatggtga | 260 | 20 | 12 |
| RX-0028 | ctcaggtggcttgtcagggc | 48 | 20 | 13 |
| RX-0029 | ctcgtgagactagagagaag | 111 | 20 | 14 |
| RX-0030 | aagtccagaggtgggggtgc | 145 | 20 | 15 |
| RX-0031 | gagatctggctgcatctc | 331 | 18 | 16 |
| RX-0032 | gaactcacattatgtggaag | 398 | 20 | 17 |
| RX-0033 | cacagaggccttatcaagat | 422 | 20 | 18 |
| RX-0034 | tagctgatggtaagcctcat | 442 | 20 | 19 |
| RX-0035 | ccagcatccagaagtttcct | 472 | 20 | 20 |
| RX-0036 | catcttcaatatccaaatca | 492 | 20 | 21 |
| RX-0037 | attcatctgtgctttcatgt | 512 | 20 | 22 |
| RX-0038 | catgtcaccatcatctgtga | 572 | 20 | 23 |
| RX-0039 | gtatttgttcacattatcag | 602 | 20 | 24 |
| RX-0040 | cactgtgtccagttagttca | 639 | 20 | 25 |
| RX-0041 | catggtcacatggatgagta | 669 | 20 | 26 |
| RX-0042 | taagcatttctctcatttcc | 690 | 20 | 27 |
| RX-0043 | ttcacaaggccatttctgtg | 712 | 20 | 28 |
| RX-0044 | ttagggtacacttcattctg | 771 | 20 | 29 |
| RX-0045 | tatgttcatagttcttcctc | 797 | 20 | 30 |
| RX-0046 | atacctttccatgttgcagac | 819 | 20 | 31 |
| RX-0047 | aatgagccaccagtgtccaa | 2772 | 20 | 2 |
| RX-0048 | ataaatagactgctttaggt | 2782 | 20 | 32 |
| RX-0049 | cagtattgtagccaggcttc | 2832 | 20 | 33 |
| RX-0050 | ttgaactaaccaagtttgtg | 2852 | 20 | 34 |
| RX-0051 | gctgtctgtgatccagcatt | 2928 | 20 | 35 |
| RX-0052 | atgctactgcaatgcaatgg | 2976 | 20 | 36 |
| RX-0053 | aaaggttactgccttcttac | 3091 | 20 | 37 |
| RX-0054 | tcaactgcctatgatcatga | 3113 | 20 | 38 |
| RX-0055 | gtactgctggcaaagcatta | 3173 | 20 | 39 |
| RX-0056 | attccatgagtaactgctgg | 3233 | 20 | 40 |
| RX-0057 | gattaacaatgtcatgttcc | 3320 | 20 | 41 |

TABLE 2-continued

List of HIF-1 S-Oligonucleotides

| ID | 5'-Sequence-3' | start | length | Sequence Id. # |
|---|---|---|---|---|
| RX-0058 | ataataaaccatacagcatt | 3358 | 20 | 42 |
| RX-0059 | tattatgtaaatggctttac | 3386 | 20 | 43 |
| RX-0060 | ttctagatatatgcatatct | 3411 | 20 | 44 |
| RX-0061 | atcagatgatttctctgaat | 3463 | 20 | 45 |
| RX-0062 | aacttccacaactacatagg | 3523 | 20 | 46 |
| RX-0063 | gtttaatatcagttacacaa | 3543 | 20 | 47 |
| RX-0064 | tataccaacagggtaggcag | 3582 | 20 | 48 |
| RX-0065 | ctgccttgtataggagcatt | 2671 | 20 | 49 |
| RX-0066 | caccctgcagtaggtttctg | 2691 | 20 | 50 |
| RX-0067 | taacttgatccaaagctctg | 2721 | 20 | 51 |
| RX-0068 | aaaattagatgtagaaaata | 2811 | 20 | 52 |
| RX-0069 | agtagaaaggggatcaaaaa | 2872 | 20 | 53 |
| RX-0070 | aaagagcattaatgtaaatt | 2893 | 20 | 54 |
| RX-0071 | ccaaaaaactgagaaaatga | 2948 | 20 | 55 |
| RX-0072 | aaattatattggcatcttct | 3069 | 20 | 56 |
| RX-0073 | attgtgcaattgtggctacc | 3195 | 20 | 9 |
| RX-0074 | atttcttcttaaaaactagt | 3271 | 20 | 57 |
| RX-0075 | ggtttaacaatttcataggc | 3299 | 20 | 58 |
| RX-0076 | ccaaataaatgccacatacc | 3431 | 20 | 59 |
| RX-0077 | tttgagctggcaaagtgact | 3491 | 20 | 60 |
| RX-0078 | tcttgtttacagtctgctca | 3611 | 20 | 61 |
| RX-0079 | atgcttctaaaattactcaa | 3751 | 20 | 62 |
| RX-0080 | aacaagatatttactgtgac | 3791 | 20 | 63 |
| RX-0081 | cagttagtgttagatccaacc | 3857 | 20 | 64 |
| RX-0082 | ataaaaggtgcattttttta | 3001 | 20 | 65 |
| RX-0083 | ccctagccaaaaataaataa | 3021 | 20 | 66 |
| RX-0084 | attcgaaaaagggataaact | 3041 | 20 | 67 |
| RX-0085 | aaaaggtgtaaaaattttc | 3131 | 20 | 68 |
| RX-0086 | atttatgtaaaatgtgaaaa | 3151 | 20 | 69 |
| RX-0087 | aattttgctaagaatgcatg | 3641 | 20 | 70 |
| RX-0088 | agcaaattaacatactaggc | 3661 | 20 | 71 |
| RX-0089 | aaatcaaacattgtatttg | 3681 | 20 | 72 |
| RX-0090 | taatagcg acaaagtgcata | 3701 | 20 | 73 |
| RX-0091 | ctacatgaaaaaaaggatgt | 3721 | 20 | 74 |
| RX-0092 | aactatatattcctaaaata | 3771 | 20 | 75 |
| RX-0117 | tgaatgtggcctgtgcagtg | 841 | 20 | 76 |
| RX-0118 | tgaggttggttactgttggt | 871 | 20 | 77 |

TABLE 2-continued

List of HIF-1 S-Oligonucleotides

| ID | 5'-Sequence-3' | start | length | Sequence Id. # |
|---|---|---|---|---|
| RX-0119 | cagcaccaagcaggtcatag | 911 | 20 | 78 |
| RX-0120 | tcttctggctcatatcccat | 1051 | 20 | 79 |
| RX-0121 | ttggtcagatgatcagagtc | 1111 | 20 | 80 |
| RX-0122 | tgtcctgtggtgacttgtcc | 1156 | 20 | 81 |
| RX-0123 | acccagacatatccacctct | 1195 | 20 | 82 |
| RX-0124 | tggttgagaattcttggtgt | 1241 | 20 | 83 |
| RX-0125 | ttcacacatacaatgcactg | 1261 | 20 | 84 |
| RX-0126 | tgctgaataataccactcac | 1288 | 20 | 85 |
| RX-0127 | aggacacattctgtttgttg | 1327 | 20 | 86 |
| RX-0128 | ttcatatctgaagattcaac | 1354 | 20 | 87 |
| RX-0129 | tcaactttggtgaatagctg | 1381 | 20 | 88 |
| RX-0130 | ggctacttgtatcttctgat | 1401 | 20 | 89 |
| RX-0131 | catcaggttccttcttaagt | 1431 | 20 | 90 |
| RX-0132 | gctgggccagcaaagttaa | 1453 | 20 | 91 |
| RX-0133 | agatatgattgtgtctccag | 1475 | 20 | 92 |
| RX-0134 | ctggtcatcagtttctgtgt | 1514 | 20 | 93 |
| RX-0135 | aatggtacttcctcaagttg | 1534 | 20 | 94 |
| RX-0136 | atttatattctgtaatttt | 1586 | 20 | 95 |
| RX-0137 | ggtaatggagacattgccaa | 1606 | 20 | 96 |
| RX-0138 | gtgcagggtcagcactactt | 1653 | 20 | 97 |
| RX-0139 | taatgcaacttcttgattga | 1673 | 20 | 98 |
| RX-0140 | ctctggatttggttctaatt | 1694 | 20 | 99 |
| RX-0141 | gtaaagaaagttccagtga | 1714 | 20 | 100 |
| RX-0142 | tgtctgatcctgaatctggg | 1739 | 20 | 101 |
| RX-0143 | actttgtctagtgcttccat | 1772 | 20 | 102 |
| RX-0144 | ggactattaggctcaggtga | 1792 | 20 | 103 |
| RX-0145 | gaccatatcactatccacat | 1829 | 20 | 104 |
| RX-0146 | ccaattccaacttgaattca | 1851 | 20 | 105 |
| RX-0147 | gttctttgcttctgtgtctt | 1889 | 20 | 106 |
| RX-0148 | taaatctgtgtcctgagtag | 1916 | 20 | 107 |
| RX-0149 | ggagctaacatctccaagtc | 1936 | 20 | 4 |
| RX-0150 | tgctttctaatggtgacaac | 2001 | 20 | 108 |
| RX-0151 | aactgtgctttgaggacttg | 2042 | 20 | 109 |
| RX-0152 | tgagtctgctggaatactgt | 2062 | 20 | 110 |
| RX-0153 | ttagcagtaggttcttgtat | 2083 | 20 | 111 |
| RX-0154 | ttaattcatcagtggtggca | 2118 | 20 | 112 |
| RX-0155 | atattttaatgtcttccata | 2157 | 20 | 113 |
| RX-0156 | aggagatggagatgcaatca | 2177 | 20 | 114 |
| RX-0157 | gtttctttatgtatgtgggt | 2197 | 20 | 115 |
| RX-0158 | gtgatgatgtggcactagta | 2217 | 20 | 10 |
| RX-0159 | actttgagtatctctatatg | 2237 | 20 | 116 |
| RX-0160 | ctctgttttggtgaggctgtc | 2258 | 20 | 117 |
| RX-0161 | ctgtctgttctatgactcct | 2286 | 20 | 118 |
| RX-0162 | tagggcttcttggatgagat | 2310 | 20 | 119 |
| RX-0163 | ttcctcaggaactgtagttc | 2357 | 20 | 120 |
| RX-0164 | attctgcaaagctagtatct | 2390 | 20 | 121 |
| RX-0165 | agtgaaccatcatgttccat | 2428 | 20 | 122 |
| RX-0166 | tccaattcctactgcttgaa | 2440 | 20 | 123 |
| RX-0167 | tctggctgctgtaataatgt | 2470 | 20 | 124 |
| RX-0168 | tgatgtagtagctgcatgat | 2492 | 20 | 125 |
| RX-0169 | tagatttgcatccttttaca | 2526 | 20 | 126 |
| RX-0170 | cagtctacatgctaaatcag | 2591 | 20 | 127 |
| RX-0171 | tcatccattgattgcccag | 2611 | 20 | 128 |
| RX-0172 | tcagctgtggtaatccactt | 2631 | 20 | 129 |
| RX-0173 | aacttcacaatcataactgg | 2651 | 20 | 130 |

FIG. 1 shows down-regulation of HIF-1 mRNA level in 13 cancer cell lines (UMRC2, OVCAR-3, MKN-45, A549, PC3, U251, Lox IMVI, HeLa, HepG2, HT-29, Caki-1, PANC-1 and MCF-7) after transfection with 0.3 μM RX-0047 and RX-0149. High level down-regulation of HIF-1 was observed in UMRC2, PANC-1, OVCAR-3, MCF-7, Lox IMVI, A549 and PC3 cell lines, moderate level down-regulation was observed in HT-29 and Caki-1 cells, and low level down-regulation was observed in HeLa, HepG2, MKN45, and U251. As shown in FIG. 1, the level of down-regulation of HIF-1 mRNA expression by RX-0047 and RX-0149 was similar except RX-0047-treated cells showed little higher level of down-regulation than RX-0149-treated in a few cell lines.

Example 5

Western Blot Analysis of HIF-1 Protein Levels

Various cancer cell lines were transfected as described above in Example 3 with the preferred RX-0047 and RX-0149 oligonucleotides at a concentration of 0.3 μM. Cells were treated with an iron-chelator, deferroxiamine at 100 uM final concentration 6 hour prior to 24 hour post-transfection. For nuclear extract preparation, the following method was used. For 10 cm dish, cells were washed gently with ice-cold PBS containing 0.1 mM NaVO$_4$ (2×6 ml), resuspended with 1 ml of ice-cold PBS with 0.1 mM NaVO$_4$ and centrifuged at 2000 rpm for 5 minutes. The pellet was resuspended in 0.3–0.5 ml of CE buffer, pH 7.6 (10 mM HEPES, 60 mM KCl, 1 mM EDTA, 1 mM DTT, 1 mM PMSF, 1× protease inhibitor cocktail and 0.1 mM NaVO$_4$)

with 0.5% NP40 and cells were allowed to swell on ice for 5 minutes. The preparation was spun at 2000 rpm for 5 minutes. The cytoplasmic extract was removed from the pellet and transferred to a new tube. The nuclei were washed gently with 0.5 ml of CE buffer without NP40. The nuclei were centrifuged as above at 2,000 rpm for 5 minutes. 50 µl of NE buffer, pH 8.0 (20 mM Tris-HCl, 420 mM NaCl, 1.5 mM $MgCl_2$, 0.2 mM EDTA, 1 mM PMSF, 25% glycerol, 0.1 mM $NaVO_4$, and 1× protease inhibitor cocktail) was added to nuclear pellet and vortexed to resuspend the pellet. The extract was incubated on ice for 40 minutes with a periodic vortexing to resuspend the pellet and the CE and NE fractions were spun at maximum speed for 15 minutes to pellet any nuclei. The supernatant was transferred to a new tube (soluble nuclear fraction) and stored at −70° C. BCA protein assay reagent (Pierce Biotechnology, Rockford, Ill.) was used to measure protein concentration. Crude cell extracts were used to determine HIF-1 protein expression by SDS-PAGE and subsequent Western analysis using an anti-HIF1 antibody (Transduction Labs, Lexington, Ky.). Anti-beta-actin antibody (Santa Cruz Biotechnology) was used as an internal control. Results are shown in FIG. 2. Both RX-0047 and RX-0149 demonstrated inhibition of HIF-1 protein expression, to a greater or lesser degree in all cell lines.

Example 6

Cell Cytotoxicity Test

Human cancer cell lines were used to test cell cytotoxicity of experimental oligonucleotides. Sulforhodamine B ("SRB") method [Skehan et al., *J. National Cancer Institute*, 82: 1107–1112 (1990)] was used to assess the cell survival after RX-oligonucleotide transfection.

Cells were plated onto a 96-well plate and transfected with the oligonucleotides the next day. Following a 72-hour incubation period, the surviving cells were stained with sulforhodamine B and measured using a microplate reader. Briefly, 1,000–10,000 cells were plated onto each well in a 96-well plate and transfected with experimental oligomers using Lipofectamine 2000 reagent (Invitrogen). After 4 hour incubation, the transfection agent was removed and the fresh media were added to each well. After 72 hours incubation, media were removed. Cells were fixed with 10% trichloroacetic acid ("TCA"), incubated for 1 hour at 4° C., and washed 4 times with tap water. Subsequently cells were stained with 0.4% sulforhodamine B in 1% acetic acid for 30 minutes, washed 4 times with 1% acetic acid, and air-dried again. After 5 minutes agitation in 10 mM Tris solution, optical density of the samples was read at 530 nm using Benchmark Plus Microplate reader (Bio-Rad Laboratories, Hercules, Calif.).

The experimental compounds which showed down-regulation of HIF-1 mRNA, were used to test their effect on UMRC2 cell viability. The following oligo compounds, RX-0047, RX-0073, RX-0149 and RX-0158 were used for cytotoxicity test. RX-0047 and RX-0149 showed the most potent cell cytotoxic effect compared with the other oligonucleotides tested. Interestingly RX-0118 and RX-0121, new oligonucleotides that had exhibited 74 and 45% inhibition of mRNA respectively, did not exhibit as much cytotoxicity as RX-0047 and RX-0149. Therefore, the test for mRNA inhibition did not correlate with cytotoxicity.

The two best candidates from mRNA inhibition studies, RX-0047 and RX-0149, were screened for cytotoxicity against a variety of cancer cell lines. RX-0047 reduced cell viability in the following human cancer cell lines; PC3 (prostate), U251 (brain), HeLa (cervix), OVCAR-3 (ovary), Lox IMVI (melanoma), HepG2 (liver), MCF-7 (breast), UMRC2 (kidney), MKN-45 (stomach), PANC-1 (pancreas), HT-29 (colon), Caki-1 (kidney) and A549 (lung). The cell cytotoxicity of RX-0047 increased with the concentration of RX-0047 among different cell lines tested. 0.1 µM of RX-0047 caused more than 50% cell death in all 13 cell lines tested. Similar results were obtained for RX-0149. Again, cytotoxicity of RX-0149 was demonstrated in all cell lines, and it increased with concentration to varying degrees among the different cell lines. 0.1 µM of RX-0149 in PC3, U251, HeLa, OVCAR-3, Lox IMVI, MCF-7, MKN-45, A549, Caki-1 and UMRC2 caused more than 50% of cell death. But more than 50% of cells in PANC-1, HT-29 and HepG2 survived at 0.1 µM.

Example 7

$IC_{50}$ Measurement of Cell Cytotoxicity for RX-0047 and RX-0149 Oligonucleotides The experimental oligonucleotides were screened for relative effective dosage. Thirteen different cancer cell lines were transfected with RX-0047 or RX-0149 at concentrations ranging from 0.01 µM to 1 µM and after 72 hours post-transfection, cells were stained with sulforhodamine B and the number of surviving cells were counted using Bio-Rad Microplate reader (Bio-Rad Laboratories). The $IC_{50}$ value, or concentration of drug needed to kill half the cells, was calculated using the KaleidaGraph Software (Synergy Software, Reading, Pa.) program. The results are reported in Table 3, below.

TABLE 3

| Cell | $IC_{50}$ (nM) | | | | | | | | | | | | |
|---|---|---|---|---|---|---|---|---|---|---|---|---|---|
| | PC3 | U251 | HeLa | OVCAR3- | Lox-IMVI | HepG2 | MCF 7 | UMRC2 | MKN-45 | A549 | Caki-1 | HT-29 | PANC-1 |
| RX-0047 | 39 | 6 | 15 | 3 | 26 | 31 | 14 | 8 | 10 | 6 | 15 | 82 | 18 |
| RX-0149 | 115 | 12 | 29 | 7 | 83 | 113 | 22 | 17 | 26 | 12 | 23 | 500 | 100 |

For comparison, it is noted that the $IC_{50}$ for UMRC2 is 8 nM for RX-0047 and 17 nM for RX-0149. Similar level of cytotoxic effect was observed in U251, OVCAR-3, and A549 cell lines.

Example 8

Sequence Variability

In order to determine whether the full 20-mer backbone of RX-0047 and RX-0149 are required to down-regulate HIF-1 mRNA expression, 18-, 16-, 14-, and 10-mer oligonucleotides were synthesized and their effects on mRNA expression and cytotoxicity were analyzed. RT-PCR analysis data indicated that the 18-mer version of RX-0047 showed some inhibition of HIF-1 mRNA expression. Whereas the 16- and 14- and 10-mer versions showed less stronger inhibition of HIF-1 mRNA expression. This suggests that the sequence truncation of RX-0047 down to 16-, 14- and 10-mer did have some effect on the desired inhibition of HIF-1 mRNA expression. For RX-0149, the 18- and 16-mer versions of RX-0149 showed similar inhibition of HIF-1 mRNA expression as the 20-mer version of RX-0149. However, when the sequence was truncated to the 14-, and 10-mer versions of RX-0149, the inhibition became insignificant. This indicates that for RX-0047, the 18- and 16-mer versions also worked as efficiently as the 20-mer version. For RX-0149, the 20-mer full-length sequence is required to achieve the maximum inhibition of HIF-1 mRNA expression.

In conjunction with the above data, we observed that oligomers comprising either 5 or 10 nucleotides, both upstream and downstream from the sequence where the 20-mer of RX-0047 was derived, showed a measurable inhibition of HIF-1 mRNA expression.

Cytotoxicity was tested using the same oligomers comprising 5 or 10 nucleotides upstream and downstream from the sequence where 20-mer of RX-0047 was derived in UMRC2 cell line. All 4 modified oligomers demonstrated cytotoxic effects comparable to the 20-mer of RX-0047, consistent with the RT-PCR data. The truncated versions of RX-0047 and RX-0149 described above also showed a similar inhibition pattern of cancer cell proliferation as observed in RT-PCR analysis.

Example 9

Ex Vivo Xenograft Study

In order to observe the inhibition of growth of tumors using one of the presently invented compounds, RX-0047, in animal models, an ex vivo xenograft study of nude mice was conducted. The A549 human lung cancer cell line was grown in a 4:1 mixture of Dulbecco's modified Eagle's medium and medium 199 supplemented with 10% cosmic calf serum (HyClone, Logan, Utah). Cells were maintained at 37° C. under 5% $CO_2$.

A marker gene, luciferase, was introduced into tumor cells. The following methods were utilized. Cells were infected with luciferase using a lentiviral vector containing the luciferase gene and a G418/neo selection marker. Cells were incubated for 24 hours in the presence of viral supernatant. Media was changed following the infection, and the G418 selection was initiated 3–4 days following the infection. Luciferase-positive cells were confirmed using a luminometer.

Immunodeficient mice (Nu/Nu; Harlan Sprague Dawley, Inc., Indianapolis, Ind.) were maintained in pathogen-free conditions within the animal resources center (ARC) at University of Texas Southwestern Medical Center and treated according to ARC and IACUC guidelines.

For the A549 lung cancer xenograft model, cells ($4 \times 10^6$ cells) were injected subcutaneously into both flanks of each mouse. Test articles were administered for 14 days via Alzet pump system. Alzet micro-osmotic pumps (Alza, Palo Alto, Calif.) were implanted subcutaneously (sc) for 10 g mice and intraperitoneally (IP) for 20 g mice. Pumping rate was maintained at 0.25 μl/hr (±0.05 μl/hr) with continuous infusion for 14 days. Sterile technique was used during filling and handling of the pump and surgical implantation.

For the A549 lung cancer metastasis model, mice were γ-irradiated and $1 \times 10^6$ cells were introduced intravenously through the tail vein. Animals were imaged using luciferase-based bioluminescence imaging each week. Mice were terminated either based on negative results (after 3–4 months) or were imaged each week until the tumor burden exceeded 10% of the host animal's normal body weight (1–2 cm in diameter for an adult mouse) per ARC/IACUC guidelines.

Table 4 shows the measurement of luciferase-base bioluminescence as an indicator of tumor growth in control and RX-0047-treated athymic nude mice sc-implanted with A549 human lung carcinoma xenografts. One week following RX-0047 treatment, 3-fold reduction in tumor size was observed compared to the control animals. Two weeks following RX-0047 treatment, a 2-fold reduction in tumor size was observed. This indicates that RX-0047 is a potent anti-tumor agent in tumor xenograft model.

TABLE 4

| Treatment | rlu* (1 week after treatment) | rlu* (2 weeks after treatment) |
|---|---|---|
| Control | $2.0 \times 10^8$ | $3.8 \times 10^8$ |
| RX-0047, 30 mg/kg/day | $5.8 \times 10^7$ | $1.7 \times 10^8$ | rlu* = relative light units

In the A549 metastasis model, animals were treated with daily IP doses of RX-0047 (60 mg/kg/day for 9 days followed by 30 mg/kg/day for additional 5 days). The imaging of the metastatic tumor was performed at 2 and 3 weeks following 14-days of RX-0047 IP administration. As shown in Table 5, 2 weeks post treatment with RX-0047, the lung metastasis was not detected while lung metastasis in the control group was observed. Three weeks following RX-0047 treatment, lung metastasis was decreased 60-fold as compared to the control group. This indicates that RX-0047 is potentially a strong inhibitor of lung metastases.

TABLE 5

| Treatment | rlu* (2 week after treatment) | rlu* (3 weeks after treatment) |
|---|---|---|
| Control | $1.9 \times 10^7$ | $7.7 \times 10^7$ |
| RX-0047 | 0 | $1.3 \times 10^6$ | rlu* = relative light units

What is claimed is:

1. A composition comprising the oligonucleotide of Seq. Id. No. 2, wherein said oligonucleotide is targeted to a nucleic acid molecule encoding human HIF-1, and wherein said oligonucleotide inhibits the expression of human HIF-1.

2. The composition of claim 1, wherein the oligonucleotide is an antisense oligonucleotide.

3. The antisense oligonucleotide of claim 2 having at least one modified internucleoside linkage that is a phosphorothioate linkage.

4. A method of inhibiting the expression HIF-1 in human cells or tissues comprising contacting said cells or tissues with the composition of claim 1.

5. A method of inducing cytotoxicity in a cancer cell comprising the step of introducing into the cell a composition comprising an oligonucleotide of Seq. Id. No. 2 that hybridizes to a human HIF-1 sequence.

* * * * *

SEQUENCE LISTING

<160> NUMBER OF SEQ ID NOS: 130

<210> SEQ ID NO 1
<211> LENGTH: 20
<212> TYPE: DNA

```
<213> ORGANISM: human

<400> SEQUENCE: 1
ttggacactg gtggctcatt                                               20

<210> SEQ ID NO 2
<211> LENGTH: 20
<212> TYPE: DNA
<213> ORGANISM: artificial sequence
<220> FEATURE:
<223> OTHER INFORMATION: antisense oligonucleotide

<400> SEQUENCE: 2
aatgagccac cagtgtccaa                                               20

<210> SEQ ID NO 3
<211> LENGTH: 20
<212> TYPE: DNA
<213> ORGANISM: human

<400> SEQUENCE: 3
gacttggaga tgttagctcc                                               20

<210> SEQ ID NO 4
<211> LENGTH: 20
<212> TYPE: DNA
<213> ORGANISM: artificial sequence
<220> FEATURE:
<223> OTHER INFORMATION: antisense oligonucleotide

<400> SEQUENCE: 4
ggagctaaca tctccaagtc                                               20

<210> SEQ ID NO 5
<211> LENGTH: 18
<212> TYPE: DNA
<213> ORGANISM: artificial sequence
<220> FEATURE:
<223> OTHER INFORMATION: primer

<400> SEQUENCE: 5
gcacaggcca cattcacg                                                 18

<210> SEQ ID NO 6
<211> LENGTH: 23
<212> TYPE: DNA
<213> ORGANISM: artificial sequence
<220> FEATURE:
<223> OTHER INFORMATION: primer

<400> SEQUENCE: 6
tgaagattca accggtttaa gga                                           23

<210> SEQ ID NO 7
<211> LENGTH: 20
<212> TYPE: DNA
<213> ORGANISM: artificial sequence
<220> FEATURE:
<223> OTHER INFORMATION: primer

<400> SEQUENCE: 7
cccatgccat cctgcgtctg                                               20

<210> SEQ ID NO 8
<211> LENGTH: 19
```

```
<212> TYPE: DNA
<213> ORGANISM: artificial sequence
<220> FEATURE:
<223> OTHER INFORMATION: primer

<400> SEQUENCE: 8
acggagtact tgcgctcag                                            19

<210> SEQ ID NO 9
<211> LENGTH: 20
<212> TYPE: DNA
<213> ORGANISM: artificial sequence
<220> FEATURE:
<223> OTHER INFORMATION: Antisense oligonucleotide

<400> SEQUENCE: 9
attgtgcaat tgtggctacc                                           20

<210> SEQ ID NO 10
<211> LENGTH: 20
<212> TYPE: DNA
<213> ORGANISM: artificial sequence
<220> FEATURE:
<223> OTHER INFORMATION: antisense oligonucleotide

<400> SEQUENCE: 10
gtgatgatgt ggcactagta                                           20

<210> SEQ ID NO 11
<211> LENGTH: 20
<212> TYPE: DNA
<213> ORGANISM: artificial sequence
<220> FEATURE:
<223> OTHER INFORMATION: antisense oligonucleotide

<400> SEQUENCE: 11
ctccatggtg aatcggtccc                                           20

<210> SEQ ID NO 12
<211> LENGTH: 20
<212> TYPE: DNA
<213> ORGANISM: artificial sequence
<220> FEATURE:
<223> OTHER INFORMATION: antisense oligonucleotide

<400> SEQUENCE: 12
gccggcgccc tccatggtga                                           20

<210> SEQ ID NO 13
<211> LENGTH: 20
<212> TYPE: DNA
<213> ORGANISM: artificial sequence
<220> FEATURE:
<223> OTHER INFORMATION: antisense ologonucleotide

<400> SEQUENCE: 13
ctcaggtggc ttgtcagggc                                           20

<210> SEQ ID NO 14
<211> LENGTH: 20
<212> TYPE: DNA
<213> ORGANISM: artificial sequence
<220> FEATURE:
<223> OTHER INFORMATION: antisense oligonucleotide

<400> SEQUENCE: 14
```

```
ctcgtgagac tagagagaag                                               20
```

<210> SEQ ID NO 15
<211> LENGTH: 20
<212> TYPE: DNA
<213> ORGANISM: artificial sequence
<220> FEATURE:
<223> OTHER INFORMATION: antisense oligonucleotide

<400> SEQUENCE: 15

```
aagtccagag gtgggggtgc                                               20
```

<210> SEQ ID NO 16
<211> LENGTH: 18
<212> TYPE: DNA
<213> ORGANISM: artificial sequence
<220> FEATURE:
<223> OTHER INFORMATION: antisense oligonucleotide

<400> SEQUENCE: 16

```
gagatctggc tgcatctc                                                 18
```

<210> SEQ ID NO 17
<211> LENGTH: 20
<212> TYPE: DNA
<213> ORGANISM: artificial sequence
<220> FEATURE:
<223> OTHER INFORMATION: antisense oligonucleotide

<400> SEQUENCE: 17

```
gaactcacat tatgtggaag                                               20
```

<210> SEQ ID NO 18
<211> LENGTH: 20
<212> TYPE: DNA
<213> ORGANISM: artificial sequence
<220> FEATURE:
<223> OTHER INFORMATION: antisense oligonucleotide

<400> SEQUENCE: 18

```
cacagaggcc ttatcaagat                                               20
```

<210> SEQ ID NO 19
<211> LENGTH: 20
<212> TYPE: DNA
<213> ORGANISM: artificial sequence
<220> FEATURE:
<223> OTHER INFORMATION: antisense oligonucleotide

<400> SEQUENCE: 19

```
tagctgatgg taagcctcat                                               20
```

<210> SEQ ID NO 20
<211> LENGTH: 20
<212> TYPE: DNA
<213> ORGANISM: artificial sequence
<220> FEATURE:
<223> OTHER INFORMATION: antisense oligonucleotide

<400> SEQUENCE: 20

```
ccagcatcca gaagtttcct                                               20
```

<210> SEQ ID NO 21
<211> LENGTH: 20
<212> TYPE: DNA
<213> ORGANISM: artificial sequence

```
<220> FEATURE:
<223> OTHER INFORMATION: antisense oligonucleotide

<400> SEQUENCE: 21
catcttcaat atccaaatca                                              20

<210> SEQ ID NO 22
<211> LENGTH: 20
<212> TYPE: DNA
<213> ORGANISM: artificial sequence
<220> FEATURE:
<223> OTHER INFORMATION: antisense oligonucleotide

<400> SEQUENCE: 22
attcatctgt gctttcatgt                                              20

<210> SEQ ID NO 23
<211> LENGTH: 20
<212> TYPE: DNA
<213> ORGANISM: artificial sequence
<220> FEATURE:
<223> OTHER INFORMATION: antisense oligonucleotide

<400> SEQUENCE: 23
catgtcacca tcatctgtga                                              20

<210> SEQ ID NO 24
<211> LENGTH: 20
<212> TYPE: DNA
<213> ORGANISM: artificial sequence
<220> FEATURE:
<223> OTHER INFORMATION: antisense oligonucleotide

<400> SEQUENCE: 24
gtatttgttc acattatcag                                              20

<210> SEQ ID NO 25
<211> LENGTH: 20
<212> TYPE: DNA
<213> ORGANISM: artificial sequence
<220> FEATURE:
<223> OTHER INFORMATION: antisense oligonucleotide

<400> SEQUENCE: 25
cactgtgtcc agttagttca                                              20

<210> SEQ ID NO 26
<211> LENGTH: 20
<212> TYPE: DNA
<213> ORGANISM: artificial sequence
<220> FEATURE:
<223> OTHER INFORMATION: antisense oligonucleotide

<400> SEQUENCE: 26
catggtcaca tggatgagta                                              20

<210> SEQ ID NO 27
<211> LENGTH: 20
<212> TYPE: DNA
<213> ORGANISM: artificial sequence
<220> FEATURE:
<223> OTHER INFORMATION: antisense oligonucleotide

<400> SEQUENCE: 27
taagcatttc tctcatttcc                                              20
```

<210> SEQ ID NO 28
<211> LENGTH: 20
<212> TYPE: DNA
<213> ORGANISM: artificial sequence
<220> FEATURE:
<223> OTHER INFORMATION: antisense oligonucleotide

<400> SEQUENCE: 28
ttcacaaggc catttctgtg                                              20

<210> SEQ ID NO 29
<211> LENGTH: 20
<212> TYPE: DNA
<213> ORGANISM: artificial sequence
<220> FEATURE:
<223> OTHER INFORMATION: antisense oligonucleotide

<400> SEQUENCE: 29
ttagggtaca cttcattctg                                              20

<210> SEQ ID NO 30
<211> LENGTH: 20
<212> TYPE: DNA
<213> ORGANISM: artificial sequence
<220> FEATURE:
<223> OTHER INFORMATION: antisense oligonucleotide

<400> SEQUENCE: 30
tatgttcata gttcttcctc                                              20

<210> SEQ ID NO 31
<211> LENGTH: 20
<212> TYPE: DNA
<213> ORGANISM: artificial sequence
<220> FEATURE:
<223> OTHER INFORMATION: antisense oligonucleotide

<400> SEQUENCE: 31
ataccttcca tgttgcagac                                              20

<210> SEQ ID NO 32
<211> LENGTH: 20
<212> TYPE: DNA
<213> ORGANISM: artificial sequence
<220> FEATURE:
<223> OTHER INFORMATION: antisense oligonucleotide

<400> SEQUENCE: 32
ataaatagac tgctttaggt                                              20

<210> SEQ ID NO 33
<211> LENGTH: 20
<212> TYPE: DNA
<213> ORGANISM: artificial sequence
<220> FEATURE:
<223> OTHER INFORMATION: antisense oligonucleotide

<400> SEQUENCE: 33
cagtattgta gccaggcttc                                              20

<210> SEQ ID NO 34
<211> LENGTH: 20
<212> TYPE: DNA
<213> ORGANISM: artificial sequence
<220> FEATURE:
<223> OTHER INFORMATION: antisense oligonucleotide

```
<400> SEQUENCE: 34
ttgaactaac caagtttgtg                                               20

<210> SEQ ID NO 35
<211> LENGTH: 20
<212> TYPE: DNA
<213> ORGANISM: artificial sequence
<220> FEATURE:
<223> OTHER INFORMATION: antisense oligonucleotide

<400> SEQUENCE: 35
gctgtctgtg atccagcatt                                               20

<210> SEQ ID NO 36
<211> LENGTH: 20
<212> TYPE: DNA
<213> ORGANISM: artificial sequence
<220> FEATURE:
<223> OTHER INFORMATION: antisense oligonucleotide

<400> SEQUENCE: 36
atgctactgc aatgcaatgg                                               20

<210> SEQ ID NO 37
<211> LENGTH: 20
<212> TYPE: DNA
<213> ORGANISM: artificial sequence
<220> FEATURE:
<223> OTHER INFORMATION: antisense oligonucleotide

<400> SEQUENCE: 37
aaaggttact gccttcttac                                               20

<210> SEQ ID NO 38
<211> LENGTH: 20
<212> TYPE: DNA
<213> ORGANISM: artificial sequence
<220> FEATURE:
<223> OTHER INFORMATION: antisense oligonucleotide

<400> SEQUENCE: 38
tcaactgcct atgatcatga                                               20

<210> SEQ ID NO 39
<211> LENGTH: 20
<212> TYPE: DNA
<213> ORGANISM: artificial sequence
<220> FEATURE:
<223> OTHER INFORMATION: antisense oligonucleotide

<400> SEQUENCE: 39
gtactgctgg caaagcatta                                               20

<210> SEQ ID NO 40
<211> LENGTH: 20
<212> TYPE: DNA
<213> ORGANISM: artificial sequence
<220> FEATURE:
<223> OTHER INFORMATION: antisense oligonucleotide

<400> SEQUENCE: 40
attccatgag taactgctgg                                               20

<210> SEQ ID NO 41
```

```
<211> LENGTH: 20
<212> TYPE: DNA
<213> ORGANISM: artificial sequence
<220> FEATURE:
<223> OTHER INFORMATION: antisense oligonucleotide

<400> SEQUENCE: 41
gattaacaat gtcatgttcc                                              20

<210> SEQ ID NO 42
<211> LENGTH: 20
<212> TYPE: DNA
<213> ORGANISM: artificial sequence
<220> FEATURE:
<223> OTHER INFORMATION: antisense oligonucleotide

<400> SEQUENCE: 42
ataataaacc atacagcatt                                              20

<210> SEQ ID NO 43
<211> LENGTH: 20
<212> TYPE: DNA
<213> ORGANISM: artificial sequence
<220> FEATURE:
<223> OTHER INFORMATION: antisense oligonucleotide

<400> SEQUENCE: 43
tattatgtaa atggctttac                                              20

<210> SEQ ID NO 44
<211> LENGTH: 20
<212> TYPE: DNA
<213> ORGANISM: artificial sequence
<220> FEATURE:
<223> OTHER INFORMATION: antisense oligonucleotide

<400> SEQUENCE: 44
ttctagatat atgcatatct                                              20

<210> SEQ ID NO 45
<211> LENGTH: 20
<212> TYPE: DNA
<213> ORGANISM: artificial sequence
<220> FEATURE:
<223> OTHER INFORMATION: antisense oligonucleotide

<400> SEQUENCE: 45
atcagatgat ttctctgaat                                              20

<210> SEQ ID NO 46
<211> LENGTH: 20
<212> TYPE: DNA
<213> ORGANISM: artificial sequence
<220> FEATURE:
<223> OTHER INFORMATION: antisense oligonucleotide

<400> SEQUENCE: 46
aacttccaca actacatagg                                              20

<210> SEQ ID NO 47
<211> LENGTH: 20
<212> TYPE: DNA
<213> ORGANISM: artificial sequence
<220> FEATURE:
<223> OTHER INFORMATION: antisense oligonucleotide

<400> SEQUENCE: 47
```
gtttaatatc agttacacaa　　　　　　　　　　　　　　　　　　　　　20

<210> SEQ ID NO 48
<211> LENGTH: 20
<212> TYPE: DNA
<213> ORGANISM: artificial sequence
<220> FEATURE:
<223> OTHER INFORMATION: antisense oligonucleotide

<400> SEQUENCE: 48
tataccaaca gggtaggcag　　　　　　　　　　　　　　　　　　　　　20

<210> SEQ ID NO 49
<211> LENGTH: 20
<212> TYPE: DNA
<213> ORGANISM: artificial sequence
<220> FEATURE:
<223> OTHER INFORMATION: antisense oligonucleotide

<400> SEQUENCE: 49
ctgccttgta taggagcatt　　　　　　　　　　　　　　　　　　　　　20

<210> SEQ ID NO 50
<211> LENGTH: 20
<212> TYPE: DNA
<213> ORGANISM: artificial sequence
<220> FEATURE:
<223> OTHER INFORMATION: antisense oligonucleotide

<400> SEQUENCE: 50
caccctgcag taggtttctg　　　　　　　　　　　　　　　　　　　　　20

<210> SEQ ID NO 51
<211> LENGTH: 20
<212> TYPE: DNA
<213> ORGANISM: artificial sequence
<220> FEATURE:
<223> OTHER INFORMATION: antisense oligonucleotide

<400> SEQUENCE: 51
taacttgatc caaagctctg　　　　　　　　　　　　　　　　　　　　　20

<210> SEQ ID NO 52
<211> LENGTH: 20
<212> TYPE: DNA
<213> ORGANISM: artificial sequence
<220> FEATURE:
<223> OTHER INFORMATION: antisense oligonucleotide

<400> SEQUENCE: 52
aaaattagat gtagaaaata　　　　　　　　　　　　　　　　　　　　　20

<210> SEQ ID NO 53
<211> LENGTH: 20
<212> TYPE: DNA
<213> ORGANISM: artificial sequence
<220> FEATURE:
<223> OTHER INFORMATION: antisense oligonucleotide

<400> SEQUENCE: 53
agtagaaagg ggatcaaaaa　　　　　　　　　　　　　　　　　　　　　20

<210> SEQ ID NO 54
<211> LENGTH: 20
<212> TYPE: DNA

```
<213> ORGANISM: artificial sequence
<220> FEATURE:
<223> OTHER INFORMATION: antisense oligonucleotide

<400> SEQUENCE: 54
aaagagcatt aatgtaaatt                                              20

<210> SEQ ID NO 55
<211> LENGTH: 20
<212> TYPE: DNA
<213> ORGANISM: artificial sequence
<220> FEATURE:
<223> OTHER INFORMATION: antisense oligonucleotide

<400> SEQUENCE: 55
ccaaaaaact gagaaaatga                                              20

<210> SEQ ID NO 56
<211> LENGTH: 20
<212> TYPE: DNA
<213> ORGANISM: artificial sequence
<220> FEATURE:
<223> OTHER INFORMATION: antisense oligonucleotide

<400> SEQUENCE: 56
aaattatatt ggcatcttct                                              20

<210> SEQ ID NO 57
<211> LENGTH: 20
<212> TYPE: DNA
<213> ORGANISM: artificial sequence
<220> FEATURE:
<223> OTHER INFORMATION: antisense oligonucleotide

<400> SEQUENCE: 57
atttcttctt aaaaactagt                                              20

<210> SEQ ID NO 58
<211> LENGTH: 20
<212> TYPE: DNA
<213> ORGANISM: artificial sequence
<220> FEATURE:
<223> OTHER INFORMATION: antisense oligonucleotide

<400> SEQUENCE: 58
ggtttaacaa tttcataggc                                              20

<210> SEQ ID NO 59
<211> LENGTH: 20
<212> TYPE: DNA
<213> ORGANISM: artificial sequence
<220> FEATURE:
<223> OTHER INFORMATION: antisense oligonucleotide

<400> SEQUENCE: 59
ccaaataaat gccacatacc                                              20

<210> SEQ ID NO 60
<211> LENGTH: 20
<212> TYPE: DNA
<213> ORGANISM: artificial sequence
<220> FEATURE:
<223> OTHER INFORMATION: antisense oligonucleotide

<400> SEQUENCE: 60
tttgagctgg caaagtgact                                              20
```

<210> SEQ ID NO 61
<211> LENGTH: 20
<212> TYPE: DNA
<213> ORGANISM: artificial sequence
<220> FEATURE:
<223> OTHER INFORMATION: antisense oligonucleotide

<400> SEQUENCE: 61
tcttgtttac agtctgctca                                         20

<210> SEQ ID NO 62
<211> LENGTH: 20
<212> TYPE: DNA
<213> ORGANISM: artificial sequence
<220> FEATURE:
<223> OTHER INFORMATION: antisense oligonucleotide

<400> SEQUENCE: 62
atgcttctaa aattactcaa                                         20

<210> SEQ ID NO 63
<211> LENGTH: 20
<212> TYPE: DNA
<213> ORGANISM: artificial sequence
<220> FEATURE:
<223> OTHER INFORMATION: antisense oligonucleotide

<400> SEQUENCE: 63
aacaagatat ttactgtgac                                         20

<210> SEQ ID NO 64
<211> LENGTH: 21
<212> TYPE: DNA
<213> ORGANISM: artificial sequence
<220> FEATURE:
<223> OTHER INFORMATION: antisense oligonucleotide

<400> SEQUENCE: 64
cagttagtgt tagatccaac c                                       21

<210> SEQ ID NO 65
<211> LENGTH: 20
<212> TYPE: DNA
<213> ORGANISM: artificial sequence
<220> FEATURE:
<223> OTHER INFORMATION: antisense oligonucleotide

<400> SEQUENCE: 65
ataaaaaggt gcatttttta                                         20

<210> SEQ ID NO 66
<211> LENGTH: 20
<212> TYPE: DNA
<213> ORGANISM: artificial sequence
<220> FEATURE:
<223> OTHER INFORMATION: antisense oligonucleotide

<400> SEQUENCE: 66
ccctagccaa aaataaataa                                         20

<210> SEQ ID NO 67
<211> LENGTH: 20
<212> TYPE: DNA
<213> ORGANISM: artificial sequence
<220> FEATURE:

```
<223> OTHER INFORMATION: antisense oligonucleotide

<400> SEQUENCE: 67
attcgaaaaa gggataaact                                               20

<210> SEQ ID NO 68
<211> LENGTH: 20
<212> TYPE: DNA
<213> ORGANISM: artificial sequence
<220> FEATURE:
<223> OTHER INFORMATION: antisense oligonucleotide

<400> SEQUENCE: 68
aaaaggtgta aaaatttttc                                               20

<210> SEQ ID NO 69
<211> LENGTH: 20
<212> TYPE: DNA
<213> ORGANISM: artificial sequence
<220> FEATURE:
<223> OTHER INFORMATION: antisense oligonucleotide

<400> SEQUENCE: 69
atttatgtaa aatgtgaaaa                                               20

<210> SEQ ID NO 70
<211> LENGTH: 20
<212> TYPE: DNA
<213> ORGANISM: artificial sequence
<220> FEATURE:
<223> OTHER INFORMATION: antisense oligonucleotide

<400> SEQUENCE: 70
aattttgcta agaatgcatg                                               20

<210> SEQ ID NO 71
<211> LENGTH: 20
<212> TYPE: DNA
<213> ORGANISM: artificial sequence
<220> FEATURE:
<223> OTHER INFORMATION: antisense oligonucleotide

<400> SEQUENCE: 71
agcaaattaa catactaggc                                               20

<210> SEQ ID NO 72
<211> LENGTH: 20
<212> TYPE: DNA
<213> ORGANISM: artificial sequence
<220> FEATURE:
<223> OTHER INFORMATION: antisense oligonucleotide

<400> SEQUENCE: 72
aaatcaaaca ttgtattttg                                               20

<210> SEQ ID NO 73
<211> LENGTH: 20
<212> TYPE: DNA
<213> ORGANISM: artificial sequence
<220> FEATURE:
<223> OTHER INFORMATION: antisense oligonucleotide

<400> SEQUENCE: 73
taatagcgac aaagtgcata                                               20
```

```
<210> SEQ ID NO 74
<211> LENGTH: 20
<212> TYPE: DNA
<213> ORGANISM: artificial sequence
<220> FEATURE:
<223> OTHER INFORMATION: antisense oligonucleotide

<400> SEQUENCE: 74
ctacatgaaa aaaaggatgt                                              20

<210> SEQ ID NO 75
<211> LENGTH: 20
<212> TYPE: DNA
<213> ORGANISM: artificial sequence
<220> FEATURE:
<223> OTHER INFORMATION: antisense oligonucleotide

<400> SEQUENCE: 75
aactatatat tcctaaaata                                              20

<210> SEQ ID NO 76
<211> LENGTH: 20
<212> TYPE: DNA
<213> ORGANISM: artificial sequence
<220> FEATURE:
<223> OTHER INFORMATION: antisense oligonucleotide

<400> SEQUENCE: 76
tgaatgtggc ctgtgcagtg                                              20

<210> SEQ ID NO 77
<211> LENGTH: 20
<212> TYPE: DNA
<213> ORGANISM: artificial sequence
<220> FEATURE:
<223> OTHER INFORMATION: antisense oligonucleotide

<400> SEQUENCE: 77
tgaggttggt tactgttggt                                              20

<210> SEQ ID NO 78
<211> LENGTH: 20
<212> TYPE: DNA
<213> ORGANISM: artificial sequence
<220> FEATURE:
<223> OTHER INFORMATION: antisense oligonucleotide

<400> SEQUENCE: 78
cagcaccaag caggtcatag                                              20

<210> SEQ ID NO 79
<211> LENGTH: 20
<212> TYPE: DNA
<213> ORGANISM: artificial sequence
<220> FEATURE:
<223> OTHER INFORMATION: antisense oligonucleotide

<400> SEQUENCE: 79
tcttctggct catatcccat                                              20

<210> SEQ ID NO 80
<211> LENGTH: 20
<212> TYPE: DNA
<213> ORGANISM: artificial sequence
<220> FEATURE:
<223> OTHER INFORMATION: antisense oligonucleotide
```

```
<400> SEQUENCE: 80
ttggtcagat gatcagagtc                                               20

<210> SEQ ID NO 81
<211> LENGTH: 20
<212> TYPE: DNA
<213> ORGANISM: artificial sequence
<220> FEATURE:
<223> OTHER INFORMATION: antisense oligonucleotide

<400> SEQUENCE: 81
tgtcctgtgg tgacttgtcc                                               20

<210> SEQ ID NO 82
<211> LENGTH: 20
<212> TYPE: DNA
<213> ORGANISM: artificial sequence
<220> FEATURE:
<223> OTHER INFORMATION: antisense oligonucleotide

<400> SEQUENCE: 82
acccagacat atccacctct                                               20

<210> SEQ ID NO 83
<211> LENGTH: 20
<212> TYPE: DNA
<213> ORGANISM: artificial sequence
<220> FEATURE:
<223> OTHER INFORMATION: antisense oligonucleotide

<400> SEQUENCE: 83
tggttgagaa ttcttggtgt                                               20

<210> SEQ ID NO 84
<211> LENGTH: 20
<212> TYPE: DNA
<213> ORGANISM: artificial sequence
<220> FEATURE:
<223> OTHER INFORMATION: antisense oligonucleotide

<400> SEQUENCE: 84
ttcacacata caatgcactg                                               20

<210> SEQ ID NO 85
<211> LENGTH: 20
<212> TYPE: DNA
<213> ORGANISM: artificial sequence
<220> FEATURE:
<223> OTHER INFORMATION: antisense oligonucleotide

<400> SEQUENCE: 85
tgctgaataa taccactcac                                               20

<210> SEQ ID NO 86
<211> LENGTH: 20
<212> TYPE: DNA
<213> ORGANISM: artificial sequence
<220> FEATURE:
<223> OTHER INFORMATION: antisense oligonucleotide

<400> SEQUENCE: 86
aggacacatt ctgtttgttg                                               20

<210> SEQ ID NO 87
<211> LENGTH: 20
```

```
<212> TYPE: DNA
<213> ORGANISM: artificial sequence
<220> FEATURE:
<223> OTHER INFORMATION: antisense oligonucleotide

<400> SEQUENCE: 87
ttcatatctg aagattcaac                                                    20

<210> SEQ ID NO 88
<211> LENGTH: 20
<212> TYPE: DNA
<213> ORGANISM: artificial sequence
<220> FEATURE:
<223> OTHER INFORMATION: antisense oligonucleotide

<400> SEQUENCE: 88
tcaactttgg tgaatagctg                                                    20

<210> SEQ ID NO 89
<211> LENGTH: 20
<212> TYPE: DNA
<213> ORGANISM: artificial sequence
<220> FEATURE:
<223> OTHER INFORMATION: antisense oligonucleotide

<400> SEQUENCE: 89
ggctacttgt atcttctgat                                                    20

<210> SEQ ID NO 90
<211> LENGTH: 20
<212> TYPE: DNA
<213> ORGANISM: artificial sequence
<220> FEATURE:
<223> OTHER INFORMATION: antisense oligonucleotide

<400> SEQUENCE: 90
catcaggttc cttcttaagt                                                    20

<210> SEQ ID NO 91
<211> LENGTH: 20
<212> TYPE: DNA
<213> ORGANISM: artificial sequence
<220> FEATURE:
<223> OTHER INFORMATION: antisense oligonucleotide

<400> SEQUENCE: 91
gctggggcca gcaaagttaa                                                    20

<210> SEQ ID NO 92
<211> LENGTH: 20
<212> TYPE: DNA
<213> ORGANISM: artificial sequence
<220> FEATURE:
<223> OTHER INFORMATION: antisense oligonucleotide

<400> SEQUENCE: 92
agatatgatt gtgtctccag                                                    20

<210> SEQ ID NO 93
<211> LENGTH: 20
<212> TYPE: DNA
<213> ORGANISM: artificial sequence
<220> FEATURE:
<223> OTHER INFORMATION: antisense oligonucleotide

<400> SEQUENCE: 93
```
ctggtcatca gtttctgtgt                                          20

<210> SEQ ID NO 94
<211> LENGTH: 20
<212> TYPE: DNA
<213> ORGANISM: artificial sequence
<220> FEATURE:
<223> OTHER INFORMATION: antisense oligonucleotide

<400> SEQUENCE: 94
aatggtactt cctcaagttg                                          20

<210> SEQ ID NO 95
<211> LENGTH: 20
<212> TYPE: DNA
<213> ORGANISM: artificial sequence
<220> FEATURE:
<223> OTHER INFORMATION: antisense oligonucleotide

<400> SEQUENCE: 95
atttatattc tgtaattttt                                          20

<210> SEQ ID NO 96
<211> LENGTH: 20
<212> TYPE: DNA
<213> ORGANISM: artificial sequence
<220> FEATURE:
<223> OTHER INFORMATION: antisense oligonucleotide

<400> SEQUENCE: 96
ggtaatggag acattgccaa                                          20

<210> SEQ ID NO 97
<211> LENGTH: 20
<212> TYPE: DNA
<213> ORGANISM: artificial sequence
<220> FEATURE:
<223> OTHER INFORMATION: antisense oligonucleotide

<400> SEQUENCE: 97
gtgcagggtc agcactactt                                          20

<210> SEQ ID NO 98
<211> LENGTH: 20
<212> TYPE: DNA
<213> ORGANISM: artificial sequence
<220> FEATURE:
<223> OTHER INFORMATION: antisense oligonucleotide

<400> SEQUENCE: 98
taatgcaact tcttgattga                                          20

<210> SEQ ID NO 99
<211> LENGTH: 20
<212> TYPE: DNA
<213> ORGANISM: artificial sequence
<220> FEATURE:
<223> OTHER INFORMATION: antisense oligonucleotide

<400> SEQUENCE: 99
ctctggattt ggttctaatt                                          20

<210> SEQ ID NO 100
<211> LENGTH: 20
<212> TYPE: DNA
<213> ORGANISM: artificial sequence

```
<220> FEATURE:
<223> OTHER INFORMATION: antisense oligonucleotide

<400> SEQUENCE: 100
gtaaaagaaa gttccagtga                                              20

<210> SEQ ID NO 101
<211> LENGTH: 20
<212> TYPE: DNA
<213> ORGANISM: artificial sequence
<220> FEATURE:
<223> OTHER INFORMATION: antisense oligonucleotide

<400> SEQUENCE: 101
tgtctgatcc tgaatctggg                                              20

<210> SEQ ID NO 102
<211> LENGTH: 20
<212> TYPE: DNA
<213> ORGANISM: artificial sequence
<220> FEATURE:
<223> OTHER INFORMATION: antisense oligonucleotide

<400> SEQUENCE: 102
actttgtcta gtgcttccat                                              20

<210> SEQ ID NO 103
<211> LENGTH: 20
<212> TYPE: DNA
<213> ORGANISM: artificial sequence
<220> FEATURE:
<223> OTHER INFORMATION: antisense oligonucleotide

<400> SEQUENCE: 103
ggactattag gctcaggtga                                              20

<210> SEQ ID NO 104
<211> LENGTH: 20
<212> TYPE: DNA
<213> ORGANISM: artificial sequence
<220> FEATURE:
<223> OTHER INFORMATION: antisense oligonucleotide

<400> SEQUENCE: 104
gaccatatca ctatccacat                                              20

<210> SEQ ID NO 105
<211> LENGTH: 20
<212> TYPE: DNA
<213> ORGANISM: artificial sequence
<220> FEATURE:
<223> OTHER INFORMATION: antisense oligonucleotide

<400> SEQUENCE: 105
ccaattccaa cttgaattca                                              20

<210> SEQ ID NO 106
<211> LENGTH: 20
<212> TYPE: DNA
<213> ORGANISM: artificial sequence
<220> FEATURE:
<223> OTHER INFORMATION: antisense oligonucleotide

<400> SEQUENCE: 106
gttctttgct tctgtgtctt                                              20
```

<210> SEQ ID NO 107
<211> LENGTH: 20
<212> TYPE: DNA
<213> ORGANISM: artificial sequence
<220> FEATURE:
<223> OTHER INFORMATION: antisense oligonucleotide

<400> SEQUENCE: 107
taaatctgtg tcctgagtag                                               20

<210> SEQ ID NO 108
<211> LENGTH: 20
<212> TYPE: DNA
<213> ORGANISM: artificial sequence
<220> FEATURE:
<223> OTHER INFORMATION: antisense oligonucleotide

<400> SEQUENCE: 108
tgctttctaa tggtgacaac                                               20

<210> SEQ ID NO 109
<211> LENGTH: 20
<212> TYPE: DNA
<213> ORGANISM: artificial sequence
<220> FEATURE:
<223> OTHER INFORMATION: antisense oligonucleotide

<400> SEQUENCE: 109
aactgtgctt tgaggacttg                                               20

<210> SEQ ID NO 110
<211> LENGTH: 20
<212> TYPE: DNA
<213> ORGANISM: artificial sequence
<220> FEATURE:
<223> OTHER INFORMATION: antisense oligonucleotide

<400> SEQUENCE: 110
tgagtctgct ggaatactgt                                               20

<210> SEQ ID NO 111
<211> LENGTH: 20
<212> TYPE: DNA
<213> ORGANISM: artificial sequence
<220> FEATURE:
<223> OTHER INFORMATION: antisense oligonucleotide

<400> SEQUENCE: 111
ttagcagtag gttcttgtat                                               20

<210> SEQ ID NO 112
<211> LENGTH: 20
<212> TYPE: DNA
<213> ORGANISM: artificial sequence
<220> FEATURE:
<223> OTHER INFORMATION: antisense oligonucleotide

<400> SEQUENCE: 112
ttaattcatc agtggtggca                                               20

<210> SEQ ID NO 113
<211> LENGTH: 20
<212> TYPE: DNA
<213> ORGANISM: artificial sequence
<220> FEATURE:
<223> OTHER INFORMATION: antisense oligonucleotide

```
<400> SEQUENCE: 113
atattttaat gtcttccata                                              20

<210> SEQ ID NO 114
<211> LENGTH: 20
<212> TYPE: DNA
<213> ORGANISM: artificial sequence
<220> FEATURE:
<223> OTHER INFORMATION: antisense oligonucleotide

<400> SEQUENCE: 114
aggagatgga gatgcaatca                                              20

<210> SEQ ID NO 115
<211> LENGTH: 20
<212> TYPE: DNA
<213> ORGANISM: artificial sequence
<220> FEATURE:
<223> OTHER INFORMATION: antisense oligonucleotide

<400> SEQUENCE: 115
gtttctttat gtatgtgggt                                              20

<210> SEQ ID NO 116
<211> LENGTH: 20
<212> TYPE: DNA
<213> ORGANISM: artificial sequence
<220> FEATURE:
<223> OTHER INFORMATION: antisense oligonucleotide

<400> SEQUENCE: 116
actttgagta tctctatatg                                              20

<210> SEQ ID NO 117
<211> LENGTH: 20
<212> TYPE: DNA
<213> ORGANISM: artificial sequence
<220> FEATURE:
<223> OTHER INFORMATION: antisense oligonucleotide

<400> SEQUENCE: 117
ctctgtttgg tgaggctgtc                                              20

<210> SEQ ID NO 118
<211> LENGTH: 20
<212> TYPE: DNA
<213> ORGANISM: artificial sequence
<220> FEATURE:
<223> OTHER INFORMATION: antisense oligonucleotide

<400> SEQUENCE: 118
ctgtctgttc tatgactcct                                              20

<210> SEQ ID NO 119
<211> LENGTH: 20
<212> TYPE: DNA
<213> ORGANISM: artificial sequence
<220> FEATURE:
<223> OTHER INFORMATION: antisense oligonucleotide

<400> SEQUENCE: 119
tagggcttct tggatgagat                                              20

<210> SEQ ID NO 120
```

```
<211> LENGTH: 20
<212> TYPE: DNA
<213> ORGANISM: artificial sequence
<220> FEATURE:
<223> OTHER INFORMATION: antisense oligonucleotide

<400> SEQUENCE: 120
ttcctcagga actgtagttc                                            20

<210> SEQ ID NO 121
<211> LENGTH: 20
<212> TYPE: DNA
<213> ORGANISM: artificial sequence
<220> FEATURE:
<223> OTHER INFORMATION: antisense oligonucleotide

<400> SEQUENCE: 121
attctgcaaa gctagtatct                                            20

<210> SEQ ID NO 122
<211> LENGTH: 20
<212> TYPE: DNA
<213> ORGANISM: artificial sequence
<220> FEATURE:
<223> OTHER INFORMATION: antisense oligonucleotide

<400> SEQUENCE: 122
agtgaaccat catgttccat                                            20

<210> SEQ ID NO 123
<211> LENGTH: 20
<212> TYPE: DNA
<213> ORGANISM: artificial sequence
<220> FEATURE:
<223> OTHER INFORMATION: antisense oligonucleotide

<400> SEQUENCE: 123
tccaattcct actgcttgaa                                            20

<210> SEQ ID NO 124
<211> LENGTH: 20
<212> TYPE: DNA
<213> ORGANISM: artificial sequence
<220> FEATURE:
<223> OTHER INFORMATION: antisense oligonucleotide

<400> SEQUENCE: 124
tctggctgct gtaataatgt                                            20

<210> SEQ ID NO 125
<211> LENGTH: 20
<212> TYPE: DNA
<213> ORGANISM: artificial sequence
<220> FEATURE:
<223> OTHER INFORMATION: antisense oligonucleotide

<400> SEQUENCE: 125
tgatgtagta gctgcatgat                                            20

<210> SEQ ID NO 126
<211> LENGTH: 20
<212> TYPE: DNA
<213> ORGANISM: artificial sequence
<220> FEATURE:
<223> OTHER INFORMATION: antisense oligonucleotide

<400> SEQUENCE: 126
```

```
tagatttgca tccttttaca                                              20

<210> SEQ ID NO 127
<211> LENGTH: 20
<212> TYPE: DNA
<213> ORGANISM: artificial sequence
<220> FEATURE:
<223> OTHER INFORMATION: antisense oligonucleotide

<400> SEQUENCE: 127
cagtctacat gctaaatcag                                              20

<210> SEQ ID NO 128
<211> LENGTH: 20
<212> TYPE: DNA
<213> ORGANISM: artificial sequence
<220> FEATURE:
<223> OTHER INFORMATION: antisense oligonucleotide

<400> SEQUENCE: 128
tcatccattg attgccccag                                              20

<210> SEQ ID NO 129
<211> LENGTH: 20
<212> TYPE: DNA
<213> ORGANISM: artificial sequence
<220> FEATURE:
<223> OTHER INFORMATION: antisense oligonucleotide

<400> SEQUENCE: 129
tcagctgtgg taatccactt                                              20

<210> SEQ ID NO 130
<211> LENGTH: 20
<212> TYPE: DNA
<213> ORGANISM: artificial sequence
<220> FEATURE:
<223> OTHER INFORMATION: antisense oligonucleotide

<400> SEQUENCE: 130
aacttcacaa tcataactgg                                              20
```